United States Patent [19]
Masuhara et al.

[11] Patent Number: 5,104,591
[45] Date of Patent: Apr. 14, 1992

[54] METHOD FOR LIGHT CURING OF DENTAL LIGHT-CURING RESINS

[75] Inventors: Eiichi Masuhara, Tokyo; Shigeo Komiya, Urawa; Shin Makino, Ichikawa, all of Japan

[73] Assignee: Japan Institute of Advanced Dentistry, Tokyo, Japan

[21] Appl. No.: 467,399

[22] Filed: Jan. 22, 1990

[30] Foreign Application Priority Data

Jan. 25, 1989 [JP] Japan ................................. 1-14011
Feb. 28, 1989 [JP] Japan ................................. 1-45133

[51] Int. Cl.$^5$ ...................... A61C 13/00; B29C 33/58
[52] U.S. Cl. ...................... 264/16; 264/22; 264/316
[58] Field of Search ...................... 264/16, 17, 22, 547, 264/570, 316, 552; 522/1, 3, 908, 915

[56] References Cited

U.S. PATENT DOCUMENTS

| | | | |
|---|---|---|---|
| 4,439,380 | 3/1984 | Michl et al. | 264/16 |
| 4,615,665 | 10/1986 | Tateosian et al. | 264/22 |
| 4,879,073 | 11/1989 | Kromrey | 264/22 |

Primary Examiner—Jan H. Silbaugh
Assistant Examiner—Christopher A. Fiorilla
Attorney, Agent, or Firm—Nixon & Vanderhye

[57] ABSTRACT

Dental light-curing resins are cured with light and under pressure by placing the uncured resin on a cast or mold or dental appliance to be prepared then covered with a transparent or translucent flexible membrane or sheet. In a chamber gas pressure is applied to the sheet and, in turn, to all parts of the underlying resin and, while pressurized, the resin is exposed to light to cure it.

6 Claims, 2 Drawing Sheets

METHOD FOR LIGHT CURING OF DENTAL LIGHT-CURING RESINS

BACKGROUND OF THE INVENTION

1. Field of Invention

The present invention relates to a method and apparatus for light curing dental light-curing resins so as to improve the properties such as the surface property of the resultant cured resins.

2. Prior Art

In recent years, light-curing resins have been employed in the preparation of dental laboratory products (prostheses) for use in dentures, removable space maintainers, removable orthodontic appliances, crowns and bridges, and the like.

The light-curing resins are easier to handle and faster to polymerize than the conventional self-curing resins or heat-curing resins which require a powder and solution to be mixed with each other. It has a further advantage that the resulting product includes only a few air bubbles and has good properties since it has been in advance prepared in a one-paste form.

However, the conventional light-curing denture base resins are treated in such a manner that the resin paste is finger-pressed and fixed onto a stone cast and then light-cured. This process is time-consuming and requires much skill to obtain an air bubble-free surface with uniform thickness.

In addition, although the air bubbles within the resin paste are invisible with a naked eye, minute air bubbles have often been found arisen on the surface contacted with the stone cast when light-cured under normal pressure, because the resin paste is detached from the surface of the stone cast due to polymerization and contraction.

Accordingly, the resin prosthesis thus obtained has been deteriorated with respect to the surface property of the contacted surface with the stone cast, and its mechanical resistance is unsatisfactory.

Moreover, in the process of light curing of crown and bridge-veneering resins wherein the resin paste is built up, using an instrument, on an opaque resin surface applied to the metal surface of a facing, and then light-cured under normal pressure, contraction will take place at a laminated part between the opaque resin surface and the resin paste before the completion of the light curing of crown and bridge-veneering resins. As a result, a satisfactory adhesion strength can not be obtained.

When the resulting prosthesis is used, said laminated part will break inside the mouth. Application of adhesive primer, for example, has been tried for preventing such break, but it has proven to be an unsatisfactory solution.

Furthermore, the conventional light-curing resins tend to leave more unpolymerized layer than heat-curing resins because they are polymerized and cured at a room temperature. Thus, the cured product has poor mechanical resistance, and absorbs much water. Accordingly, it is highly soluble and lacks long-term durability inside the mouth.

SUMMARY OF THE INVENTION

In an attempt to solve disadvantages in the prior arts, the present inventors have completed the present invention, by which dental light-curing resin products having excellent properties such as a uniform well-bonding surface property can be now obtained.

An aspect of the present invention is to provide a method for light curing of dental light-curing resins, characterized in that gas pressure is exerted on the resins during the light curing.

The surface of the dental light-curing resins are preferably covered by a transparent or translucent and flexible sheet and the gas pressure is exerted through the sheet.

Preferably, the dental light-curing resins are pressed and fixed on a support and the sheet is heated before or during the light curing.

Another aspect of the present invention is to provide an apparatus for said light curing, comprising a light-curing unit equipped with a lighting unit and gas-pressure unit. The apparatus may be in a form of two-part container which is easily opened and closed.

DETAILED DESCRIPTION OF THE INVENTION

Figure 1:
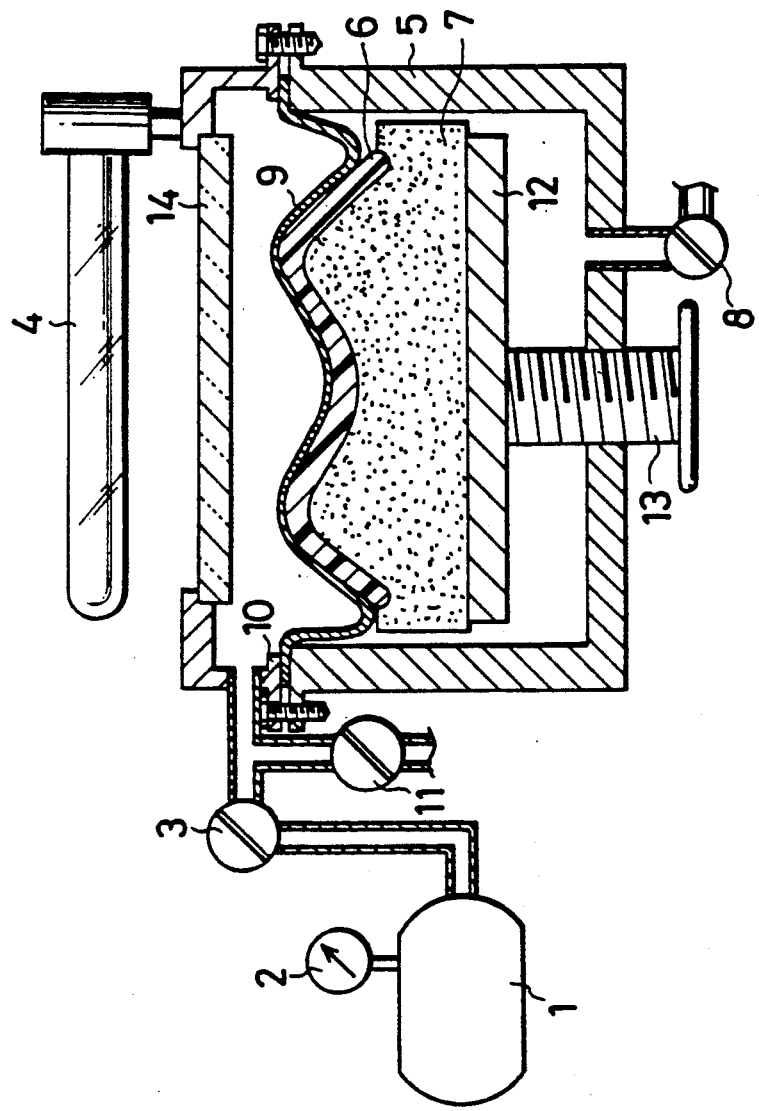
FIG. 1 shows a partial cross section of the apparatus which is used in EXAMPLE 1.
Figure 2:
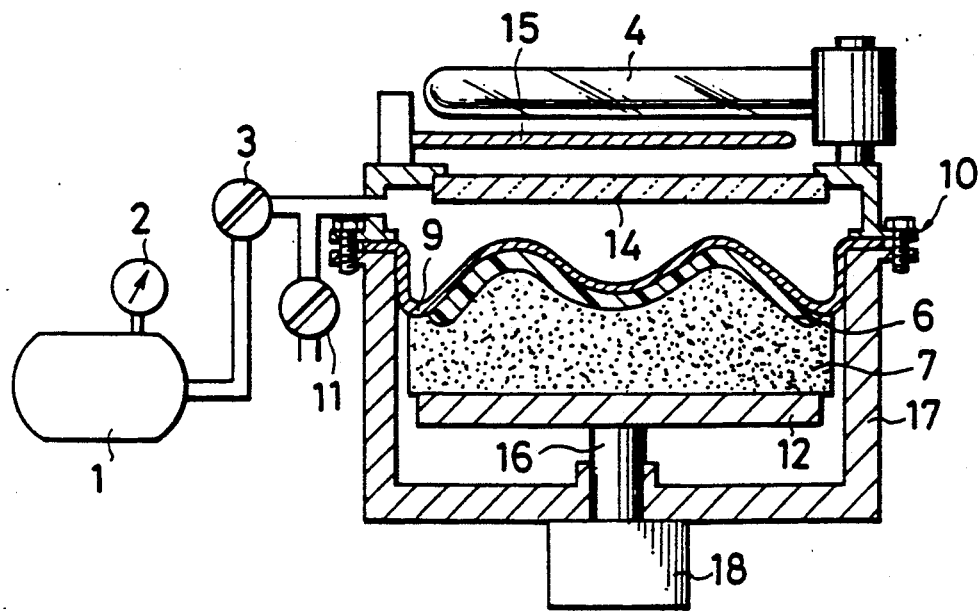
FIG. 2 shows a partial cross section of the apparatus which is used in EXAMPLE 4.
Figure 3:
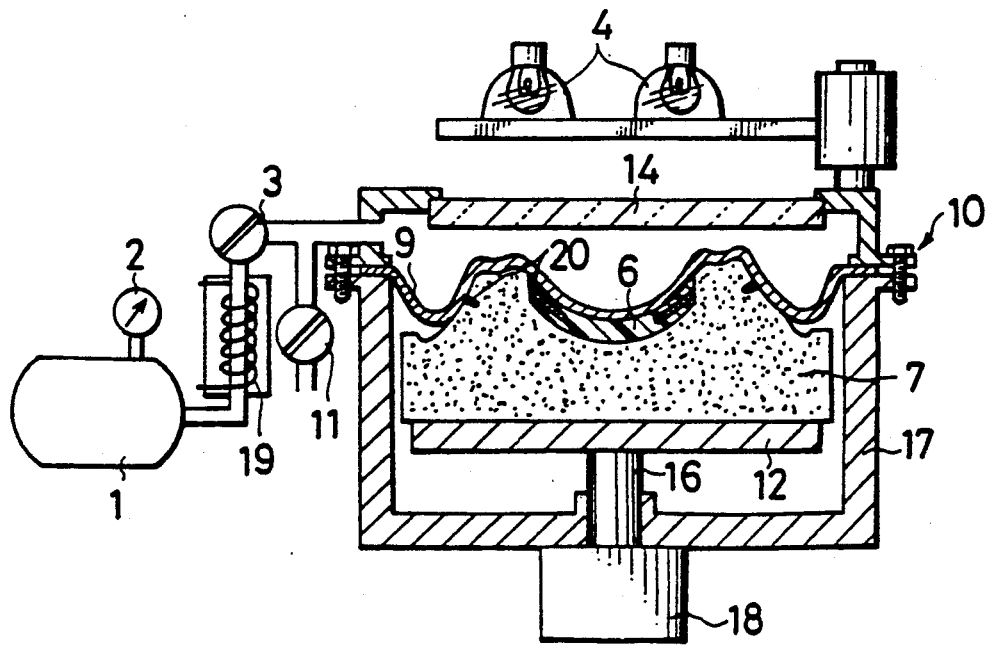
FIG. 3 shows a partial cross section of the apparatus which is used in EXAMPLE 5.

Gas pressure may be exerted, for example, by means of compressed gas provided by a compressor or gas bomb connected to the light-curing unit. The pressure and kind of gas within the unit may be optionally selected according to the user's purpose or application. When it is necessary to remain as an unpolymerized layer on the surface of the light-cured resins for successively laminating light-curing resins, air or oxygen is preferably used as the compressed gas. On the other hand, if the complete polymerization of the resin is desired, inert gas such as nitrogen, argon or helium gas is preferably used. A range of the gas pressure within the light-curing unit is not fixed, but generally it is from 1 to 20 $kg/cm^2$, preferably from 2 to 10 $kg/cm^2$. Pressure lower than 1 $kg/cm^2$ can not effectively press the resin surface, and pressure greater than 20 $kg/cm^2$ may disadvantageously press the prosthesis to be too thin. The most preferable pressure range may be from 2 to 7 $kg/cm^2$. When one presses and fixes the dental light-curing resins on the support, finger pressure is normally employed in order to evenly press on the upper surface of the resins. The support may, for example, be a stone or plaster cast, a resin cast or a denture base.

The transparent or translucent and flexible sheet may be of polyethylene, polyethylene-vinyl acetate copolymer, polyvinyl chloride, polyvinylidene chloride, polyvinylidene fluoride, polyurethane, or polysiloxane. Among them, polyvinyl chloride, polyethylene-vinyl acetate copolymer, urethane or silicon rubber is especially preferable, since it allows itself to be repeatedly pressed and fixed onto the light-curing resins without getting wrinkled.

Except polyurethane and polysiloxane, it is preferable to heat the sheet so as to be more flexible. As a heating unit of the present invention, an electrical resistance heater, infrared-ray heater, far infrared-ray heater, or microwave may be used. The heater may be positioned depending upon a type of the dental prosthesis. The temperature and time of heating may be optionally selected, being usually around 200° C. and for a few minutes. The heating of the sheet may be performed before or during the light curing, preferably before setting the sheet in the light curing unit.

In order to heat the sheet for adaptation, it is also preferable that the compressed gas should be heated to a temperature range from about 80° C. to 250° C. as it is supplied. Therefore, it is recommended to position the heater (e.g., electrical heater) along a gas conduit and before a valve for conducting the compressed gas.

The transparent or translucent and flexible sheet is very useful for uniformly transmitting the exerted gas pressure to all the parts of dental light-curing resins.

Said sheet is especially useful when it has to be press-fixed in a wide range on a surface of, e.g., denture bases or removable orthodontic appliances.

When the light-curing resins are light-cured while being gas-pressured through the sheet, no deformation such as curvature due to contraction of the resin caused by the light-curing will occur because the resins are pressed on thoroughly by the sheet at all times. Also, the light curing process will not be interrupted since the resin surface does not come in a direct contact with the gas such as the air.

A part for fastening the transparent or translucent and flexible sheet may be equipped in said apparatus so as to seal and fasten the edge of said sheet placed inside the light-curing unit.

As a lighting unit there may be used a lamp which preferably generates a visible light, such as a xenon lamp, halogen lamp or fluorescent lamp with a filter, if necessary, for cutting off ultraviolet and infrared rays.

Although said lamp may be placed either inside or outside of the light-curing unit, it is preferable to place it on the outside, considering the high gas pressure in the unit and durability of the lamp.

The degree of the light curing of the present invention may be controlled by adjusting distance between the light-curing resin and the light source (e.g., halogen lamp). For this purpose, either the light source or the resin may be arranged to be movable.

It is thus desirable that a part of the light-curing unit is made of transparent material so that the resins in the unit can be irradiated through the transparent material from the outside.

EXAMPLE 1

At first, a resin sheet of EPOREX-D (light-curing denture base resin by Nippon Oil and Fats Co., Ltd.) (6) was placed on top of a stone cast (7) having a shape of an edentulous jaw, evenly finger-pressed and then set on a bed plate (12).

Then a flexible silicon rubber (polysiloxane) sheet (9) was placed on a sheet fastener (10) and fixed, and after a screw height adjuster (13) was adjusted to control the position of the stone cast (7), a first air-conducting valve (8) and a second air-conducting valve (11) were closed.

Thereafter, by opening a compressed gas-conducting valve (3), compressed air in an air compressor (1) with a pressure gauge (2) was flowed into a light-curing unit (5) which was provided with a quartz glass window (14) until the gas pressure in the unit reached 5 Kg/cm$^2$. The quartz glass board may be coated with a filter agent for cutting removing infrared rays.

After closing the valve (3), the resin sheet (6) was light-cured for 5 minutes using 27W U-LINE 2 (a fluorescent lamp manufactured by TOSHIBA CORPORATION) (4) which emitted visible light with a wave length of 400-600 nm. When the light curing had been finished, the air-conducting valve (11) was opened to bring the gas pressure in the unit back to ambient pressure, and the light-cured resin denture base and stone cast were removed.

The denture base thus obtained was completely light-cured despite a short light-curing time and was very well compatible with the stone cast.

Furthermore, a contact surface of EPOREX-D (6) with the stone cast (7), that is, the interface between a tissue side of the denture base and the stone cast (7), did not contain any air bubble at all, and the contact surface looked very smooth and shiny.

COMPARATIVE EXPERIMENT 1

The resin sheet of EPOREX-D placed on the stone cast was light-cured for 10 minutes by using a visible light emitter LABOLIGHT LV-I (G-C DENTAL INDUSTRIAL CORP.) instead of U-LINE 2 without using the gas-pressure unit or the sheet.

Compatibility of the denture base thus obtained was inferior to that of EXAMPLE 1.

Furthermore, a few air bubbles were found in the interface between the denture base and the stone cast, which seemed to have been formed at the time when the resin sheet was pressed on the stone cast. The surface of the denture base looked rough.

EXAMPLE 2

At first, a light-curing resin sheet of TRIAD (Dentsply International Inc.) (6) was placed on top of the stone cast (7) provided with clasps and labial guide wire which had been set at a predetermined position, and then set on the bed plate (12).

Then the flexible silicon rubber sheet (9) was placed on the sheet fastener (10) and fixed, and after the screw height adjuster (13) was adjusted to control the position of the stone cast (7), the first air-conducting valve (8) and the second air-conducting valve (11) were closed.

Thereafter, by opening the compressed gas-conducting valve (3), compressed air in the air compressor (1) was flowed into the light-curing unit (5) which was provided with the quartz glass window (14) until the gas pressure in the unit reached 4 Kg/cm$^2$.

After closing the valve (3), the resin sheet (6) was light-cured for 3 minutes using 250 W Multi-mirror Project Lamp EXY (a halogen lamp manufactured by GENERAL ELECTRIC) (4) which emitted visible light with a wave length of 400-600 nm. When the light curing had been finished, the air-conducting valve (11) was opened to brought the gas pressure in the unit back to ambient pressure, and the retaining appliance and the stone cast were removed.

The retaining appliance thus obtained was completely light-cured despite a short light-curing time and was very well compatible with the stone cast.

Furthermore, a contact surface of TRIAD (6) with the stone cast (7), that is, the interface between the tissue side of the retaining appliance and the stone cast, did not contain any air bubble at all, and details of the surface were very well reproduced. The contact surface looked very smooth and shiny.

COMPARATIVE EXPERIMENT 2

The resin sheet of TRIAD placed on the stone cast was light-cured for 10 minutes by using a visible light emitter TRIAD II (Dentsply International Inc.) instead of Multi-mirror Project Lamp EXY without using the gas-pressure unit or the sheet.

Compatibility of the retaining appliance thus obtained was inferior to that of EXAMPLE 2.

Furthermore, many air bubbles were found at parts corresponding to rugae of palate and lingual cervical area in the interface between the retaining appliance and the stone cast, as well as around lug of the clasps and labial guide wire. It seemed that these air bubbles had been formed due to insufficient adaptation of the resin sheet. The surface of the retaining appliance looked rough.

EXAMPLE 3

At first, a resin paste of New METACOLOR (Sun Medical Co., LTD) was built upon a metal frame provided with a maxillary 3—3 bridge and supplied with details on its surface so as to complete the metal frame. The completed metal frame was then set on the bed plate (12), and the first air-conducting valve (8) and the second air-conducting valve (11) were closed.

Thereafter, by opening the compressed gas-conducting valve (3), compressed nitrogen gas in a gas bomb was let flow into the light-curing unit (5) which was provided with the quartz glass window (14) until the gas pressure in the unit reached 8 Kg/cm$^2$.

After closing the valve (3), the resin sheet (6) was light-cured for 60 seconds using 75 W CERAMAX (a xenon lamp manufactured by ILC Technology) (4) which emitted visible light with a wave length of 400–600 nm. When the light curing had been finished, the air-conducting bulb (8) was opened to bring the gas pressure in the unit back to ambient pressure, and the metal frame of the bridge was removed.

The bridge thus obtained was completely light-cured despite a short light-curing time. Since there was no unpolymerized layer on its surface, the surface could be made glossy only by polishing for a short time, without breaking the details on the surface.

Bubbles contained in the resin paste had disappeared by gas-pressure during the light curing, resulting in translucent and aesthetic facing resins of the bridge. When luted on the abutment, the resulting bridge could function very well because the metal frame was tightly adhered to the cured resins.

COMPARATIVE EXPERIMENT 3

The resin paste of New METACOLOR (Sun Medical Co., LTD) was built up on the same metal frame as in EXAMPLE 3, and irradiated for 2 minutes by a visible light emitter Dentacolor XS (Kulzer GmbH) instead of CERAMAX without exerting gas pressure.

The bridge thus obtained had unpolymerized layer on its surface, which required cumbersome grinding and polishing by using a bur in order to form the shape on the surface. Furthermore, small bubbles were found, which seemed to have been generated during the lamination of resin pastes of dentin color and enamel color. The bridge could get less aesthetic appreciation than that of EXAMPLE 3. After the bridge had been used in the mouth for a long time, there were found crack in the resin and coloring at the interface between the metal and resin which had been insufficiently adhered to the metal.

EXAMPLE 4

At first, the resin sheet of EPOREX-D (light-curing base resin by Nippon Oil and Fats Co., Ltd.) (6) was placed on top of the stone cast (7) having the shape of an edentulous jaw, evenly finger-pressed and then set on the bed plate (12).

Then a flexible polyvinyl chloride sheet (9) with 1.5 mm width was placed on the sheet fastener (10), and after a height adjuster (16) was shifted by using an elevator (18) in order to adjust the position of the stone cast, the air-conducting bulb (11) was closed. An infrared-ray heater (15) was then lighten up to heat the sheet at 200° C. for 60 seconds to make it more flexible.

Thereafter, by opening the compressed gas-conducting bulb (3), compressed air in the air compressor (1) was let flow into a light-curing unit (17) which was provided with the quartz glass board (14) until the gas pressure in the unit reached 4 Kg/cm$^2$.

After closing the bulb (3), the resin sheet (6) was light-cured for 4 minutes using 27 W U-LINE 2 (4) which emitted visible light with a wave length of 400–600 nm. When the light curing had been finished, the air-conducting bulb (11) was opened to brought the gas pressure in the unit back to ambient pressure, and the light-cured denture base and stone cast were removed.

The denture base thus obtained was completely light-cured despite a short light-curing time and was very well compatible with the stone cast. There was found no deformation on the denture base.

Furthermore, a contact surface of EPOREX-D (6) with the stone cast (7), that is, the interface between the tissue side of the denture base and the stone cast, did not contain any air bubble at all, and the contact surface looked very smooth and shiny.

COMPARATIVE EXAMPLE 4

The resin sheet of EPOREX-D placed on the stone cast was light-cured for 10 minutes by using LABO-LIGHT LV-I instead of U-LINE 2 without using the gas-pressure unit, the sheet nor the heating unit.

Compatibility of the denture base thus obtained was inferior to that of EXAMPLE 4.

Furthermore, a few air bubbles were found in the interface between the tissue side of the denture base and the stone cast, which seemed to have been formed at the time when the resin sheet was pressed on the stone cast. The surface of the denture base looked rough.

EXAMPLE 5

At first, the resin sheet of TRIAD (Dentsply International Inc.) (6) was placed on top of the stone cast (7) provided with clasps (20) and labial guide wire which had been set at a predetermined position, and then set on the bed plate (12).

Then an ethylene-vinyl acetate copolymer sheet (9) with 1 mm width was placed on the sheet fastener (10), and after the height adjuster (16) was adjusted to control the position of the stone cast (7), the air-conducting bulb (11) was closed.

Thereafter, by opening the compressed gas-conducting bulb (3), compressed air heated to 120° C. by an electrical heater (19) was let flow from the air compressor (1) into the light-curing unit (17) which was provided with the quarts glass board (14) until the gas pressure in the unit reached 3 Kg/cm$^2$.

After closing the bulb (3), the resin sheet (6) was light-cured for 2 minutes using 250 W Multi-mirror Project Lamp EXY (a halogen lamp manufactured by GENERAL ELECTRIC) (4) which emitted visible light with a wave length of 400–600 nm. When the light curing had been finished, the air-conducting bulb (11) was opened to brought the gas pressure in the unit back to ambient pressure, and the retaining appliance and stone cast were removed.

The retaining appliance thus obtained was completely light-cured despite a short light-curing time and had no deformation. It was very well compatible with the stone cast.

Furthermore, the contact surface of TRIAD (6) with the stone cast (7), that is, the interface between the tissue side of the retaining appliance and the stone cast, did not contain any air bubble at all, and details of the surface were very well reproduced. The contact surface looked very smooth and shiny.

Since resin around lug of the clasps and labial guide wire could keep enough strength and well adhered to the metal, after using in the mouth, there was found no coloring in the resin due to break or stains thereof.

COMPARATIVE EXPERIMENT 5

The resin sheet of TRIAD placed on the stone cast was light-cured for 10 minutes by using TRIAD II instead of Multi-mirror Project Lamp EXY without using the gas-pressure unit, the sheet nor the heating unit.

Compatibility of the retaining appliance thus obtained was inferior to that of EXAMPLE 5.

Furthermore, many air bubbles were found at parts corresponding to rugae of palate and lingual cervical area in the interface between the tissue side of the retaining appliance and the stone cast, as well as around lug of the clasps and labial guide wire. It seemed that these air bubbles had been formed due to insufficient pressure exerted to the resin sheet. The surface of the retaining appliance looked rough.

After using in the mouth, there were found coloring due to break or strains of the resin around lug of the clasps and labial guide wire, and strains in its tissue side.

EXAMPLE 6

Test samples prepared according to the above EXAMPLEs and COMPARATIVE EXPERIMENTs were subjected to universal testing machine for determining bending strength thereof. The size of the test samples is $2 \times 2 \times 25$ mm for EXAMPLEs 1 to 3 and COMPARATIVE EXPERIMENTs 1 to 3, and $65 \times 10 \times 2.5$ mm for EXAMPLEs 4 and 5 and COMPARATIVE EXPERIMENTs 4 and 5.

The results obtained are summarized in the following TABLE.

|  | Bending Strengths |  | Bending Strengths |
| --- | --- | --- | --- |
| EXAMPLE 1 | 1250 ($Kg/cm^2$) | COMPARATIVE 1 | 930 ($Kg/cm^2$) |
| EXAMPLE 2 | 1040 | COMPARATIVE 2 | 800 |
| EXAMPLE 3 | 1100 | COMPARATIVE 3 | 720 |
| EXAMPLE 4 | 1320 | COMPARATIVE 4 | 930 |
| EXAMPLE 5 | 1210 | COMPARATIVE 5 | 800 |

As seen from the results, the bending strengths of the cured resins prepared in EXAMPLEs of the present invention are higher than those of the corresponding COMPARATIVE EXPERIMENTs.

What is claimed is:

1. A method for light curing of dental light-curing resins under pressure in a closed system, comprising the steps of:
    (a) placing the light-curing resin on a stone cast,
    (b) covering the resin with a transparent or translucent flexible membrane having an outside surface,
    (c) applying gas pressure in a range between 2 and 20 $kg/cm^2$ to the outside surface of the flexible membrane thereby uniformly transmitting the gas pressure onto all parts of the resin underlying the flexible membrane, and, while applying pressure,
    (d) exposing the resin to light to thereby cure the resin.

2. The method according to claim 1, wherein the transparent or translucent flexible membrane is made of a thermoplastic resin.

3. The method according to claim 2, wherein the thermoplastic resin is polyvinyl chloride or ethylene-vinyl acetate copolymer.

4. The method according to claim 2, further comprising the step of heating the membrane to make it more flexible and conformable before applying the gas pressure.

5. The method according to claim 4, wherein the heating is maintained during the light curing.

6. The method according to claim 1, 2, 3, 4 or 5 wherein visible light is used to cure the resin.

* * * * *